US010054428B2

(12) United States Patent
Yokota

(10) Patent No.: US 10,054,428 B2
(45) Date of Patent: Aug. 21, 2018

(54) INNER SURFACE SHAPE MEASUREMENT DEVICE, DETECTION HEAD, AND ENDOSCOPE DEVICE

(71) Applicant: OLYMPUS CORPORATION, Tokyo (JP)

(72) Inventor: Masayoshi Yokota, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/467,161

(22) Filed: Mar. 23, 2017

(65) Prior Publication Data

US 2017/0191823 A1 Jul. 6, 2017

Related U.S. Application Data

(60) Division of application No. 14/225,638, filed on Mar. 26, 2014, now abandoned, which is a continuation of
(Continued)

(51) Int. Cl.
*G02B 11/24* (2006.01)
*G01B 11/24* (2006.01)
(Continued)

(52) U.S. Cl.
CPC ........... *G01B 11/24* (2013.01); *G01N 21/954* (2013.01); *G02B 23/2423* (2013.01); *G02B 23/2469* (2013.01)

(58) Field of Classification Search
CPC .. G01B 11/24; G01N 21/954; G02B 23/2423; G02B 23/2469
See application file for complete search history.

(56) References Cited

U.S. PATENT DOCUMENTS

| 5,440,081 | A |   | 8/1995 | Thompson |
| 5,550,331 | A |   | 8/1996 | Thompson |
| 5,790,185 | A | * | 8/1998 | Auzerais ............. E21B 47/0002 |
|   |   |   |   | 348/131 |

(Continued)

FOREIGN PATENT DOCUMENTS

| DE | 10 2008 060 621 B3 | 8/2010 |
| DE | 10 2009 043 538 A1 | 3/2011 |

(Continued)

OTHER PUBLICATIONS

International Search Report dated Nov. 8, 2011 issued in PCT/JP2011/072623.
(Continued)

*Primary Examiner* — Kara E Geisel
*Assistant Examiner* — Violeta A Prieto
(74) *Attorney, Agent, or Firm* — Scully, Scott, Murphy & Presser, P.C.

(57) ABSTRACT

An inner surface shape measurement device for measuring a shape of an inner surface of a test target, and includes a light source, an optical system which converts light emitted by the light source into a disc-shaped light beam to cause the light beam to be emitted toward an inner surface of the test target, a photography unit which captures an image of a state in which the light beam is projected on the inner surface of the test target, and a wiring which supplies power for driving the light source. The optical system, the light source and the photography unit are disposed in this order along a same axis line, and the wiring extends from the light source toward the photography unit.

18 Claims, 5 Drawing Sheets

Related U.S. Application Data application No. PCT/JP2011/072623, filed on Sep. 30, 2011.

(51) Int. Cl.
*G01N 21/954* (2006.01)
*G02B 23/24* (2006.01)

(56) References Cited

U.S. PATENT DOCUMENTS

| | | | |
|---|---|---|---|
| 5,895,927 A | 4/1999 | Brown | |
| 2002/0039186 A1* | 4/2002 | Rosenberg | G01J 3/02 356/432 |
| 2007/0191684 A1 | 8/2007 | Hirata | |
| 2011/0001984 A1* | 1/2011 | Keller | G01N 21/954 356/612 |
| 2011/0196200 A1 | 8/2011 | Glozman et al. | |
| 2011/0261366 A1 | 10/2011 | Tearney et al. | |
| 2012/0069351 A1 | 3/2012 | Glasenapp | |
| 2015/0377701 A1* | 12/2015 | Pawluczyk | G01J 3/0243 356/301 |

FOREIGN PATENT DOCUMENTS

| | | |
|---|---|---|
| EP | 0 846 840 A2 | 6/1998 |
| JP | S61-270600 A | 11/1986 |
| JP | S62-192244 U | 12/1987 |
| JP | S63-055441 A | 3/1988 |
| JP | H04-012724 A | 1/1992 |
| JP | H04-290950 A | 10/1992 |
| JP | H05-045142 A | 2/1993 |
| JP | 2007-285891 A | 11/2007 |
| JP | 2008-268240 A | 11/2008 |
| JP | 2009-069374 A | 4/2009 |
| WO | 2009/053989 A2 | 4/2009 |

OTHER PUBLICATIONS

Extended Supplementary European Search Report dated Apr. 24, 2015 from related European Application No. 11 87 3044.9.
Office Action dated Aug. 31, 2015 received in related U.S. Appl. No. 14/225,638.

* cited by examiner

INNER SURFACE SHAPE MEASUREMENT DEVICE, DETECTION HEAD, AND ENDOSCOPE DEVICE

CROSS REFERENCE TO RELATED APPLICATIONS

This application is a divisional application of U.S. application Ser. No. 14/225,638 filed Mar. 26, 2014, which is a continuation application based on PCT Patent Application No. PCT/JP2011/072623, filed Sep. 30, 2011. The contents of each of which are incorporated herein by reference.

FIELD OF THE INVENTION

The present invention relates to an inner surface shape measurement device, a detection head, and an endoscope device.

DESCRIPTION OF THE RELATED ART

A device which measures a shape of an inner surface of a tube using an ultrasonic wave or light is conventionally known. For example, a device which projects light for measurement (measurement light) on an inner surface of a tube over an entire circumference in a circumferential direction of the tube that is a measurement target and images the inner surface of the tube on which the measurement light has been projected is disclosed in Japanese Unexamined Patent Application First Publication No. S63-55441. In the device described in Japanese Unexamined Patent Application First Publication No. S63-55441, a linear bright part extending in the circumferential direction of the tube is generated in the inner surface of the tube by the measurement light. A shape of the inner surface of the tube can be measured by detecting a shape of the bright part based on an image of the inner surface of the tube which is imaged.

In Japanese Unexamined Patent Application First Publication No. S63-55441, a wiring which supplies power for driving a light source which emits the measurement light is disposed between a device for imaging the inner surface of the tube and a surface on which the measurement light has been projected. In this configuration, a part of the bright linear part is broken in a captured image. For the purpose of solving this problem, a plurality of optical fibers whose ends on the measurement light emission side are directed to an outer side in a radial direction of the tube are used in Japanese Unexamined Patent Application First Publication No. S63-55441. A device in which a plurality of optical fibers, a wiring disposed in gaps of the plurality of optical fibers, and a mirror which reflects an image of the inner surface of the tube on which the measurement light has been projected to a light-receiving portion are disposed is disclosed in Japanese Unexamined Patent Application First Publication No. S63-55441. The bright part caused by the measurement light is not broken by the wiring in the device described in Japanese Unexamined Patent Application First Publication No. S63-55441.

The present invention has been made in view of the aforementioned circumstances, and an object of the present invention is to provide a small inner surface shape measurement device having high measurement accuracy.

Further, another object of the present invention is to provide a small detection head capable of being attached to an endoscope and having high measurement accuracy, and a small endoscope device having high inner surface shape measurement accuracy.

SUMMARY OF THE INVENTION

According to a first aspect of the present invention, an inner surface shape measurement device is an inner surface shape measurement device for measuring a shape of an inner surface of a test target. The inner surface shape measurement device includes a light source; an optical system which converts light emitted by the light source into a disc-shaped light beam to cause the light beam to be emitted toward the inner surface; a photography unit which captures an image of a state in which the light beam is projected on the inner surface; and a wiring which supplies power for driving the light source. The optical system, the light source and the photography unit are disposed in this order along the same axis line, and the wiring extends from the light source toward the photography unit.

According to a second aspect of the present invention, in the inner surface shape measurement device according to the first aspect of the present invention, the photography unit may include an objective optical system whose focal point distance is greater than a distance between the light source and the photography unit.

According to a third aspect of the present invention, in the inner surface shape measurement device according to the first aspect of the present invention, the wiring may extend from the light source toward the photography unit along the axis line, and may be bent in a direction intersecting the axis line at a position apart from the photography unit by a predetermined distance.

According to a fourth aspect of the present invention, in the inner surface shape measurement device according to the first aspect of the present invention, the inner surface shape measurement device according to the present invention may further include a cylindrical member including a photography-unit-side opening disposed at a position apart from the photography unit by a predetermined distance and a light-source-side opening opened to the light source. The cylindrical member may have a central axis line extending along the axis line between the light source and the photography unit. The wiring may be inserted into the cylindrical member.

According to a fifth aspect of the present invention, in the inner surface shape measurement device according to the first aspect of the present invention, the wiring of at least positioned in a range of a view field of the photography unit may have optical transparency.

According to a sixth aspect of the present invention, in the inner surface shape measurement device according to the first aspect of the present invention, the inner surface shape measurement device according to the present invention may further include an insertion portion inserted into the test target. The insertion portion may include a main body formed in a cylindrical shape; and a detection head formed in a container-shape in which the axis line is located therein, the detection head detachably provided at an end portion of the main body. The optical system and the light source may be arranged inside the detection head.

According to a seventh aspect of the present invention, in the inner surface shape measurement device according to the sixth aspect of the present invention, the photography unit may include an objective optical system. At least a portion of optical elements constituting the objective optical system may be arranged inside the detection head.

According to an eighth aspect of the present invention, in the inner surface shape measurement device according to the seventh aspect of the present invention, a focal point distance of the objective optical system may be greater than a distance between the light source and the photography unit.

According to a ninth aspect of the present invention, in the inner surface shape measurement device according to the first aspect of the present invention, the light source may include a measurement light source which emits measurement light toward the optical system; and an illumination light source which emits illumination light for causing the photography unit to capture a bright field image of the inner surface.

According to a tenth aspect of the present invention, in the inner surface shape measurement device according to the ninth aspect of the present invention, the illumination light source may have an optical axis directed in a direction in which the axis line extends.

According to an eleventh aspect of the present invention, in the inner surface shape measurement device according to the tenth aspect of the present invention, the illumination light source may emit the illumination light toward the optical system. The optical system may reflect the illumination light in a direction intersecting the direction in which the axis line extends.

According to a twelfth aspect of the present invention, in the inner surface shape measurement device according to the ninth aspect of the present invention, the illumination light source may emit the illumination light in a direction intersecting a direction in which the axis line extends.

According to a thirteenth aspect of the present invention, in the inner surface shape measurement device according to the ninth aspect of the present invention, the photography unit may include an objective optical system whose focal point distance is greater than a distance between the light source and the photography unit.

According to a fourteenth aspect of the present invention, in the inner surface shape measurement device according to the ninth aspect of the present invention, the wiring may extend from the light source toward the photography unit along the axis line, and to be bent in a direction intersecting the axis line at a position apart from the photography unit by a predetermined distance.

According to a fifteenth aspect of the present invention, in the inner surface shape measurement device according to the ninth aspect of the present invention, the inner surface shape measurement device according to the present invention may further include a cylindrical member including a photography-unit-side opening disposed at a position apart from the photography unit by a predetermined distance, and a light-source-side opening directed to the light source. The cylindrical member may have a central axis line extending along the axis line between the light source and the photography unit. The wiring may be inserted into the cylindrical member.

According to a sixteenth aspect of the present invention, in the inner surface shape measurement device according to the ninth aspect of the present invention, the wiring of at least positioned in a range of a view field of the photography unit may have optical transparency.

According to a seventeenth aspect of the present invention, in the inner surface shape measurement device according to the ninth aspect of the present invention, the inner surface shape measurement device according to the present invention may further include an insertion portion inserted into the test target. The insertion portion may include a main body formed in a cylindrical shape; and a detection head formed in a container-shape and in which the axis line is located therein, the detection head may be detachably provided at an end portion of the main body. The optical system and the light source may be arranged inside the detection head.

According to an eighteenth aspect of the present invention, in the inner surface shape measurement device according to the seventeenth aspect of the present invention, the photography unit may include an objective optical system. At least a portion of optical elements constituting the objective optical system may be disposed inside the detection head.

According to a nineteenth aspect of the present invention, in the inner surface shape measurement device according to the eighteenth aspect of the present invention, a focal point distance of the objective optical system may be greater than a distance between the light source and the photography unit.

According to a twentieth aspect of the present invention, a detection head which is attachable to an endoscope in order to measure a shape of an inner surface of a test target includes a light source; an optical system which converts light emitted by the light source into a disc-shaped light beam to cause the light beam to be emitted toward the inner surface; a photography unit which captures an image of a state in which the light beam is projected on the inner surface; and a wiring which supplies power for driving the light source. The optical system, the light source and the photography unit are arranged in this order along the same axis line. The wiring extends from the light source toward the photography unit According to a twenty first aspect of the present invention, an endoscope device for measuring a shape of an inner surface of a test target includes an insertion portion inserted into the test target; a detection head disposed at a first end of the insertion portion; and a manipulation unit disposed at a second end of the insertion portion. The detection head includes a light source; an optical system which converts light emitted by the light source into a disc-shaped light beam to cause the light beam to be emitted toward the inner surface; a photography unit which captures an image of a state in which the light beam is projected on the inner surface; and a wiring which supplies power for driving the light source. The optical system, the light source and the photography unit are arranged in this order along the same axis line, and the wiring extends from the light source toward the photography unit.

DETAILED DESCRIPTION OF THE INVENTION

First Embodiment

Figure 1:
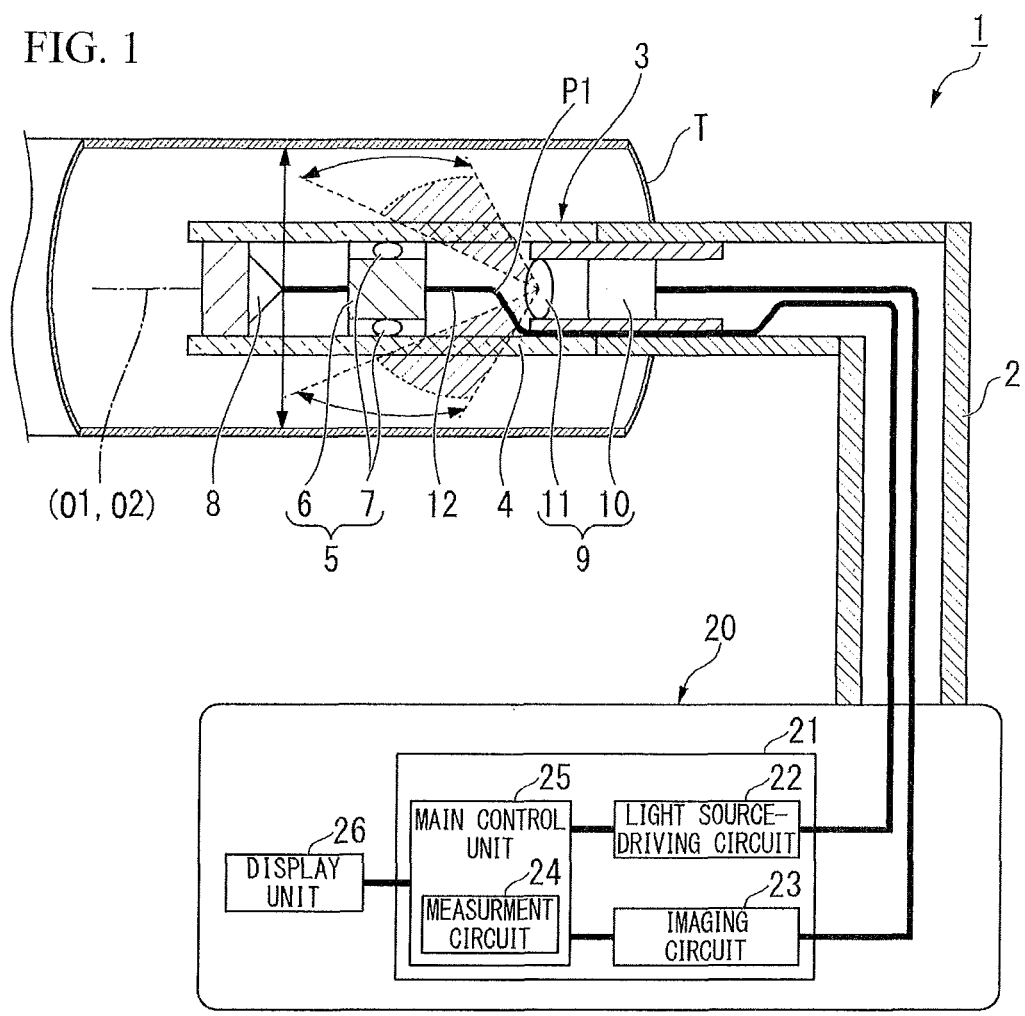
FIG. 1 is an overall view illustrating an inner surface shape measurement device according to a first embodiment of the present invention.

An inner surface shape measurement device and a detection head according to a first embodiment of the present invention will be described. FIG. 1 is an overall view illustrating the inner surface shape measurement device and the detection head according to this embodiment.

An inner surface shape measurement device 1 according to this embodiment is a device which measures a shape of an inner surface of a test target T. A shape of the test target T is not particularly limited. The inner surface shape measurement device 1 according to this embodiment is particularly suitable for measuring a shape of an inner surface of a tube having a circular cross-section. The inner surface shape measurement device 1 is configured to be able to capture a bright field image of an inside of the test target T, and has a function of a so-called endoscope device.

The inner surface shape measurement device 1 includes an insertion portion 2, a detection head 3, and a manipulation unit 20, as illustrated in FIG. 1. Further, a description will be given in this embodiment on the assumption that a side on which the detection head 3 is provided is a distal end of the inner surface shape measurement device 1, and a side on which the manipulation unit 20 is provided is a proximal end of the inner surface shape measurement device 1.

The insertion portion 2 is a longitudinal member having a cylindrical shape to be inserted into the test target T. Wirings 12 which connect the detection head 3 with the manipulation unit 20 are disposed inside the insertion portion 2. In addition, a shape of the insertion portion 2 may be set to correspond to the shape of the test target T, and the insertion portion 2 may be flexible. In this embodiment, the insertion portion 2 is a flexible tube including a flexible resin pipe and a braided wire which reinforces the resin pipe.

The detection head 3 is a container-shaped member disposed in a first end of the insertion portion 2 (a distal end of the insertion portion 2) and fixed to the insertion portion 2. The detection head 3 includes a light source 5, an optical system 8, a photography unit 9 and a wiring 12 disposed in a substantially cylindrical head frame 4. The detection head 3 is positioned such that a central axis line of the detection head 3 is coaxial with a central axis line O1 of the head frame 4 and a central axis line O2 of the insertion portion 2.

The head frame 4 is a hard cylindrical member having optical transparency. In the head frame 4, an area other than a portion on which light from the light source 5 is projected and a portion corresponding to an imaging view field of the photography unit 9 may not have the optical transparency. The light source 5 and the photography unit 9 will be described below. Although not illustrated, a support leg which supports the head frame 4 within the test target T may be provided at the head frame 4. For example, the support leg has three expansible/contractible or rotatable leg members disposed every 120° around a central axis line of the head frame 4, and is configured to be capable of positioning between a central axis line of the tube, which has a circular cross-section and the central axis line of the head frame 4.

The light source 5 includes a measurement light source 6 and an illumination light source 7. The measurement light source 6 emits measurement light toward the optical system 8. The illumination light source 7 emits illumination light for causing the photography unit 9 to capture a bright field image of an inner surface of the test target T.

The measurement light source 6 is a light source which emits the measurement light to the distal end along a central axis line of the detection head 3. For the measurement light source 6, for example, a light source which emits a laser beam may be adopted. The measurement light source 6 may be configured to emit monochromatic or white visible light.

The illumination light source 7 is configured to radiate, from an outer surface of the light source 5, the visible light in a direction intersecting a direction in which the axis line of the detection head 3 extends. In this embodiment, the illumination light source 7 includes a plurality of light-emitting diodes disposed to be spaced from one another in a circumferential direction of the detection head 3. The visible light emitted by the illumination light source 7 may be the monochromatic or white light which is different from a color of a light emitted by the measurement light source 6. The respective light-emitting diodes are disposed at equal intervals in the circumferential direction of the detection head 3. The visible light emitted by the illumination light source may be the monochromatic or white which is different color from a light emitted by the measurement light source Light-emitting states of the measurement light source 6 and the illumination light source 7 are controlled by a light source-driving circuit 22 provided at the manipulation unit 20. The light source-driving circuit 22 will be described below.

The optical system 8 includes a conic mirror which is positioned so as to be a rotating body around the central axis line of the detection head 3. A bottom surface of the conically formed optical system 8 is disposed on the distal end side of the inner surface shape measurement device 1, and a vertex of the optical system 8 is disposed on a proximal end side of the inner surface shape measurement device 1. The vertex of the conic mirror is irradiated with the light emitted by the measurement light source 6, and the light is reflected from a surface of the conic mirror. Thus, the optical system 8 converts the light emitted by the light source 5 into a disc-shaped light beam, and causes a light beam to be emitted toward the inner surface of the test target T.

In this embodiment, an angle of inclination of a side surface (a conical surface) of the conic mirror constituting the optical system 8 is 45° with respect to the bottom surface. If the angle of inclination of the side surface of the conic mirror with respect to a bottom surface of the conic mirror is smaller than 45°, the disc-shaped light beam has a disc shape spread toward the proximal end side of the detection head 3 in comparison with a case in which the angle of inclination of the conic mirror with respect to the bottom surface is 45°. On the other hand, if the angle of inclination of the side surface of the conic mirror with respect to the bottom surface is greater than 45°, the disc-shaped light beam has a disc shape spread toward the distal end side of the detection head 3 in comparison with the case in which the angle of inclination of the side surface of the conic mirror with respect to the bottom surface is 45°. Thus, the light beam may have different projection directions according to the angle of inclination of the side surface with respect to the bottom surface in the conic mirror. In the optical system 8, the angle of inclination of the side surface with respect to the bottom surface in the conic mirror may be variable.

The photography unit 9 includes an image sensor 10 such as a CCD or a CMOS, and an objective optical system 11 which causes external light to be incident on the image sensor 10. The image sensor 10 captures an image of a state in which the light beam is projected on the inner surface of the test target T, and outputs the image to an imaging circuit 23, which will be described below.

The objective optical system 11 is an optical element group whose optical axis is set along the central axis line O1 of the detection head 3. A focal point distance of the objective optical system 11 is set to be greater than a distance between the light source 5 and the photography unit 9. Therefore, when the inner surface of the test target T is photographed using the objective optical system 11, an area exceeding the distance between the light source 5 and the photography unit 9 is suitably photographed, and an object located between the light source 5 and the photography unit 9 is photographed in a state in which a focus has been blurred.

The optical system 8, the light source 5 and the photography unit 9 are disposed in this order from the distal end along the same axis line. Specifically, in this embodiment, the optical system 8, the light source 5 and the photography unit 9 are disposed along the central axis line O1 of the detection head 3 formed in a cylindrical shape, i.e., the same axis as the central axis line of the head frame 4.

The wiring 12 is provided in order to supply power for driving the light source 5. The wiring 12 includes a first end connected to the light source 5 and a second end connected to the light source-driving circuit 22 of the manipulation unit 20. In the detection head 3, the wiring 12 extends from the light source 5 toward the photography unit 9 along the central axis line O1, and is bent in the direction intersecting the central axis line O1 at a position apart from the photography unit 9 by a predetermined distance. Hereinafter, this portion is referred to as "a bent wiring portion P1." A distance between the bent wiring portion P1 and the photography unit 9 is set to a distance smaller than the focal point distance of the objective optical system 11. In this embodiment, the wiring 12 includes one wiring 12 for the illumination light source 7 and one wiring 12 for the measurement light source 6, and uses metal portions of the detection head 3 and the insertion portion 2, which are not illustrated, as a ground. Accordingly, the number of wirings 12 across the imaging view field of the photography unit 9 is a minimum number. The wiring 12 may be configured so that the light-emitting states of the illumination light source 7 and the measurement light source 6 are switched by switching polarities of the two wirings 12.

The manipulation unit 20 is disposed in the second end of the insertion portion 2 (the proximal end of the insertion portion 2). The manipulation unit 20 includes a control unit 21, and a display unit 26 connected to the control unit 21. The control unit 21 controls operation of the light source 5 and the photography unit 9 in the detection head 3.

The control unit 21 includes the light source-driving circuit 22, the imaging circuit 23, and a measurement circuit 24. The light source-driving circuit 22 controls operation of the light source 5. The imaging circuit 23 controls operation of the photography unit 9. The measurement circuit 24 performs measurement of the inner surface shape based on the image captured by the photography unit 9. In this embodiment, the measurement circuit 24 is provided as a circuit of a portion of a main control unit 25 in the inner surface shape measurement device 1.

The imaging circuit 23 forms an image based on a signal output from the image sensor 10 of the photography unit 9, and stores the image in a storage space, which is not illustrated, as an image file. A magnetic storage device, a semiconductor storage device, or the like may be appropriately selected and adopted as the storage space.

The display unit 26 displays the image formed by the imaging circuit 23 or displays a result measured by the measurement circuit 24 using letters, symbols, or other image information.

Next, operation of the inner surface shape measurement device 1 according to this embodiment will be described.

First, the detection head 3 is inserted into the inside of the test target T and guided to a desired position within the test target T by a manipulator at the time of use of the inner surface shape measurement device 1 (see FIG. 1). In this case, a bright field image of the inside of the test target T can be acquired using the photography unit 9 by causing the illumination light source 7 to emit light. The bright field image acquired by the photography unit 9 is displayed on the display unit 26. The manipulator can view the bright field image displayed on the display unit 26 to determine whether measurement is to be performed or to observe a color, a surface state or the like of the inner surface of the test target T.

If the detection head 3 reaches a position that the manipulator desires to measure, the illumination light source 7 is turned off and the measurement light source 6 is turned on. Accordingly, the measurement light is emitted from the measurement light source 6 to the distal end along the central axis line of the detection head 3. The light emitted from the measurement light source 6 is converted a disc-shaped light beam by reflecting from the surface of the conic mirror, which is the optical system 8. The disc-shaped light beam penetrates the head frame 4 and is projected on the inner surface of the test target T. When the measurement light is projected on the inner surface of the test target T, one continuous circular bright part is generated in the inner surface of the test target T.

Further, the photography unit 9 acquires an image of the inner surface of the test target T in which the bright part is generated caused by the measurement light and outputs the image to the imaging circuit 23. Accordingly, the image in a state in which the measurement light has been projected onto the position where the manipulator desires to measure is imaged. The measurement circuit 24 performs a shape measurement of the image captured by the photography unit 9. The measurement circuit 24 detects a trace of the light using a method such as binarizing the image to detect an edge of the bright part. Further, the measurement circuit 24, for example, measures the shape of the inner surface of the test target T on the light trace by using a principle of triangulation based on a position of the detected light trace.

In this embodiment, the imaging view field of the photography unit 9 is interrupted by the wiring 12. However, since the wiring 12 is provided near the objective optical system 11, it is difficult to adjust a focus to the wiring 12 when capturing the image by the photography unit 9. Accordingly, the bright part caused by the measurement light is continuous in the image captured by the photography unit 9. Therefore, in the measurement circuit 24, the light trace does not lack even when the wiring 12 interrupts the imaging view field. As a result, it is possible to perform shape measurement with high measurement accuracy even when the wiring 12 is present in the imaging view field.

As described above, the inner surface shape measurement device 1 and the detection head 3 according to this embodiment have high measurement accuracy and are small.

In this embodiment, since the focal point distance of the objective optical system 11 of the photography unit 9 is greater than the distance between the light source 5 and the photography unit 9, it is difficult to adjust the focus to the wiring 12 and it is easy to adjust the focus to the inner surface of the test target T.

In this embodiment, since the wiring 12 extends from the light source 5 toward the photography unit 9 along the central axis line O1 of the detection head 3, the wiring 12 can be disposed at a portion blocked by the light source 5 in the imaging view field of the photography unit 9. Accordingly, it is possible to reduce the wiring 12 located in the imaging view field necessary for shape measurement.

Modified Example 1-1

Figure 2:
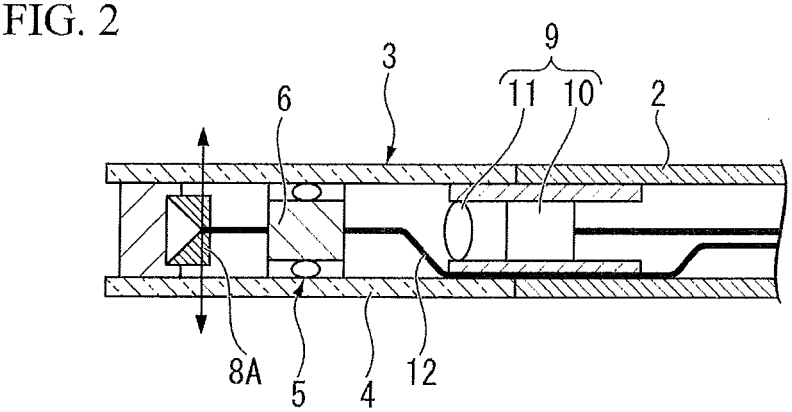
FIG. 2 is a partial cross-sectional view illustrating a modified example of the inner surface shape measurement device according to the first embodiment of the present invention.

Next, a modified example of the inner surface shape measurement device described in the above-described embodiment will be described. FIG. 2 is a partial cross-sectional view illustrating an inner surface shape measurement device of this modified example.

This modified example is different in that an optical system 8A is included in place of the optical system 8, as illustrated in FIG. 2. The optical system 8A is a conical prism in which a conically shaped hole is formed in a surface of the distal end side so as to open at the distal end side and to decrease their diameter toward the proximal end. The optical system 8A including the conical prism is fixed in a state in which a portion of the distal end is buried in a fixing portion provided at the distal end of the head frame 4.

In such a configuration, the light emitted from the measurement light source 6 is converted into a disc-shaped light beam and emitted to the inner surface of the test target T. In addition, since the prism is used, reflectance is higher than that in the first embodiment in which the reflecting mirror is used.

Modified Example 1-2

Figure 3:
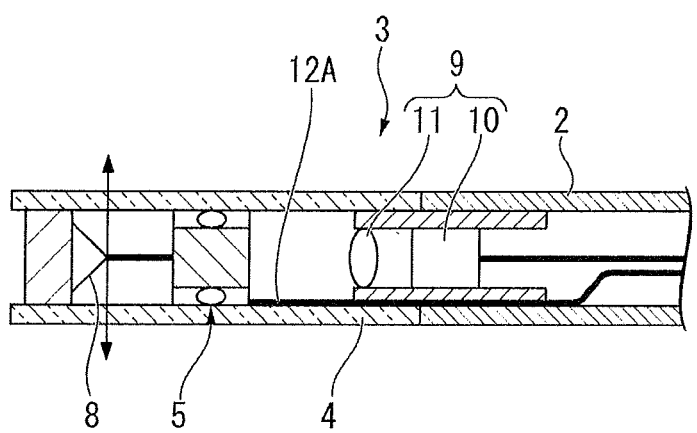
FIG. 3 is a partial cross-sectional view illustrating another modified example of the inner surface shape measurement device according to the first embodiment of the present invention.

Next, another modified example of the inner surface shape measurement device 1 described in the first embodiment will be described. FIG. 3 is a partial cross-sectional view illustrating an inner surface shape measurement device 1 of this modified example.

In this modified example, a wiring 12A having optical transparency at least in a range of the view field of the photography unit 9 is included in place of the wiring 12 described in the first embodiment, as illustrated in FIG. 3. The wiring 12A includes an optically transparent conductive film and a resin film having optical transparency. The conductive film is provided in one surface of the resin film. For the optically transparent conductive film, for example, a film containing conductive particles such as ITO (indium tin oxide) or a metal, a conductive polymer or the like may be appropriately selected and adopted.

In this modified example, since the wiring 12A has the optical transparency, it is more difficult for a bright part caused by the measurement light to be divided on the image captured by the photography unit 9 in comparison with the first embodiment when the wiring 12A is provided in a positional relationship described in the first embodiment.

The wiring 12A of this modified example having the optical transparency may be attached to an inner surface of the head frame 4. In this case, it is also difficult for the bright part caused by the measurement light to be divided.

Second Embodiment

Figure 4:
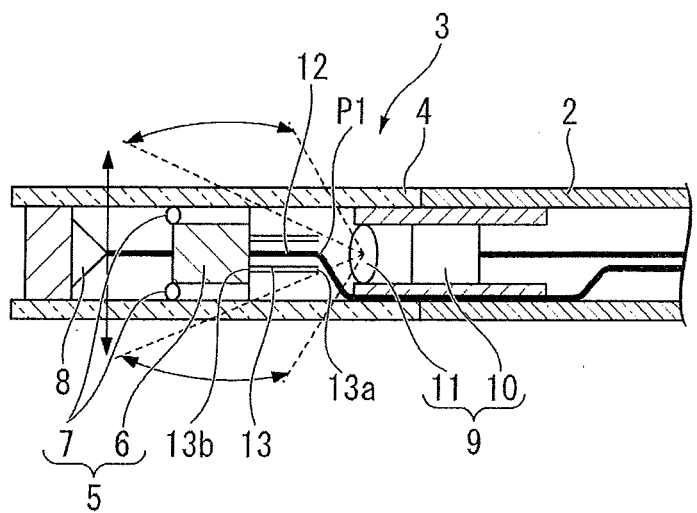
FIG. 4 is a partial cross-sectional view illustrating a partial configuration of an inner surface shape measurement device according to a second embodiment of the present invention.

Next, an inner surface shape measurement device according to a second embodiment of the present invention will be described. FIG. 4 is a partial cross-sectional view illustrating a partial configuration of an inner surface shape measurement device according to this embodiment.

The inner surface shape measurement device according to this embodiment is different in inclusion of a cylindrical member 13 and an arrangement of the illumination light source 7, as illustrated in FIG. 4. The cylindrical member 13 is disposed between the light source 5 and the photography unit 9 and provided to extend along the central axis line of the detection head 3.

The cylindrical member 13 includes a photography-unit-side opening 13a disposed at a position which is separated from the photography unit 9 by a predetermined distance, and a light-source-side opening 13b directed to the light source 5.

The position of the photography-unit-side opening 13a is set to the same position as the bent wiring portion P1 described in the first embodiment. Further, the light-source-side opening 13b is fixed to the light source 5 in this embodiment. The photography-unit-side opening 13a may come in contact with the objective optical system 11.

The wiring 12 described in the first embodiment is inserted into the cylindrical member 13.

It is preferable that a material of the cylindrical member 13 is a material having rigidity such that a central axis line of the cylindrical member 13 can be maintained on the central axis line of the detection head 3 by the fixation of the light source 5 and the cylindrical member 13.

The illumination light source 7 is disposed on the distal surface of the light source 5, unlike the first embodiment described above. Accordingly, in this embodiment, an optical axis of the illumination light source 7 is directed in a direction in which the central axis line of the detection head 3 extends. A portion of the illumination light radiated from the illumination light source 7 is reflected from the surface of the optical system 8 and is radiated in a lateral direction of the detection head 3. Accordingly, the illumination light can be irradiated the entire imaging view field of the photography unit 9 by the illumination light source 7.

In this embodiment, since the wiring 12 is supported by the cylindrical member 13, the wiring 12 is maintained in a suitable position even when the wiring 12 is made from a flexible material. In addition, since the wiring 12 can have a small diameter, the inner surface shape measurement device can be further miniaturized.

Modified Example 2-1

Figure 5:
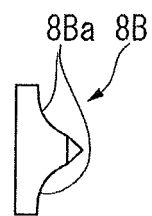
FIG. 5 is a side view illustrating a modified example of the inner surface shape measurement device according to the second embodiment of the present invention.
Figure 6:
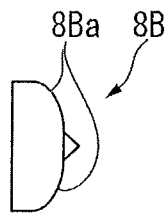
FIG. 6 is a side view illustrating another modified example of the inner surface shape measurement device according to the second embodiment of the present invention.

Next, another modified example of the inner surface shape measurement device described in the second embodiment described above will be described. FIGS. 5 and 6 are side views illustrating an optical system 8 in the inner surface shape measurement device of this modified example.

This modified example is different in that an optical system 8B having a different shape is included in place of the optical system 8 (see FIG. 1), as illustrated in FIGS. 5 and 6.

The optical system 8B has a conical shape on the proximal end side as in the second embodiment described above, and has a side surface having a curved shape on the distal end side which is different from the conical surface of the second embodiment.

The measurement light emitted by the measurement light source 6 is incident on a portion having a conical shape in the optical system 8B and is converted a disc-shaped light beam, as in the first and second embodiments. The side surface having the curved shape different from the conical surface in the optical system 8B is a light distribution portion 8Ba which reflects the illumination light emitted by the illumination light source 7 in a predetermined direction.

A shape of the light distribution portion 8Ba may be a concave surface or may be a convex surface. When the light distribution portion 8Ba is the concave surface as illustrated in FIG. 5, the light distribution portion 8Ba can change a direction of the illumination light emitted from the illumination light source 7 to a direction of an outer side in a radial direction of the detection head 3 and condense the illumination light. When the light distribution portion 8Ba is the convex surface as illustrated in FIG. 6, the light distribution portion 8Ba can change the direction of the illumination light emitted from the illumination light source 7 to the direction of the outer side in the radial direction of the detection head 3 and diffuse the illumination light.

Further, a reflection direction of the light can be changed by changing an angle of inclination of the light distribution portion 8Ba with respect to a bottom surface of the optical system 8B, as in the first embodiment described above. In this modified example, a light irradiation position and a light irradiation range can be set when the bright field image is acquired, by changing the reflection direction of the light emitted from the illumination light source 7.

Third Embodiment

Figure 7:
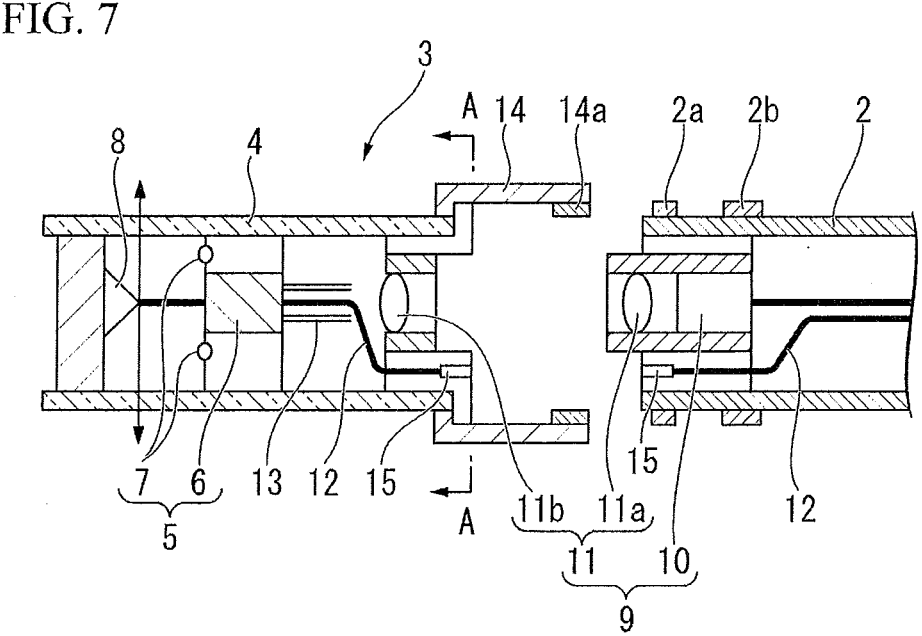
FIG. 7 is a partial cross-sectional view illustrating a partial configuration of an inner surface shape measurement device according to a third embodiment of the present invention.
Figure 8:
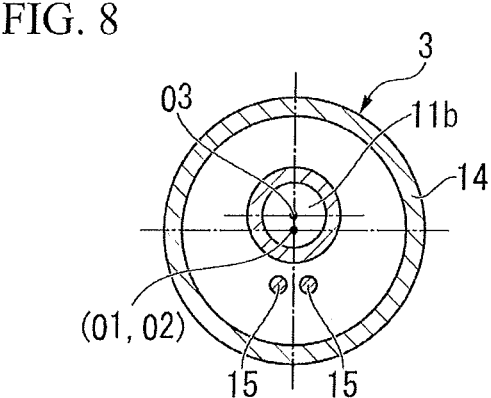
FIG. 8 is a cross-sectional view taken along a line A-A of FIG. 7.

Next, an inner surface shape measurement device according to a third embodiment of the present invention will be described. FIG. 7 is a partial cross-sectional view illustrating a partial configuration of the inner surface shape measurement device according to this embodiment. FIG. 8 is a cross-sectional view taken along a line A-A of FIG. 7.

This embodiment is different from the previous embodiments in that primary portions of the detection head 3 are detachable from the insertion portion 2, as illustrated in FIG. 7. The primary portions of the detection head 3 in this embodiment are the light source 5 and the optical system 8.

In this embodiment, two screw threads 2a and 2b formed in a spiral shape along an outer circumferential surface are provided at the distal end of the insertion portion 2. The two screw threads 2a and 2b are spaced from each other such that an interspace is formed in a longitudinal axis direction of the insertion portion 2.

A portion (a first lens portion 11a) of optical elements constituting the objective optical system 11 and the image sensor 10 are disposed inside a distal end side of the insertion portion 2.

The optical system 8 and the light source 5 which are primary portions of the detection head 3 are accommodated inside the detection head 3. Further, in this embodiment, a portion (a second lens portion 11b) of the optical elements constituting the objective optical system 11 is disposed inside the detection head 3.

A stop ring 14 is provided at the proximal end of the head frame 4. The stop ring 14 is provided to be rotatable relative to the head frame 4 around the central axis line of the detection head 3.

A screw groove 14a with which the screw threads 2a and 2b formed in the insertion portion 2 can be screwed is formed in the stop ring 14.

In this embodiment, an axis line O3 on which the optical system 8, the light source 5 and the photography unit 9 are disposed in line is set parallel to the central axis line of the head frame 4 of the detection head 3, and is offset with respect to the central axis line O1 of the head frame 4, as illustrated in FIGS. 7 and 8.

The wiring 12 is electrically connected by a pair of contact terminals 15 at a connection portion between the detection head 3 and the insertion portion 2.

In this embodiment, the detection head 3 and the insertion portion 2 are connected by screwing the stop ring 14 with the distal end of the insertion portion 2. In this case, the first lens portion 11a and the second lens portion 11b are connected in a state in which their optical axes are aligned, and function as the objective optical system 11. In addition, even when the stop ring 14 moves away from the screw thread 2b on the proximal end side among the screw threads 2a and 2b formed on the distal end of the insertion portion 2, the detection head 3 is prevented from falling out of the insertion portion 2 since the stop ring 14 is caught by the screw thread 2a on the distal end side.

When the second lens portion 11b is provided on the insertion portion 2 side, the contact terminals 15 for connecting the wiring 12 on the detection head 3 side with the wiring 12 on the insertion portion 2 side may enter the field of photography view of the photography unit 9. However, in this modified example, the second lens portion 11b which is a portion of the objective optical system 11 is disposed within the detection head 3. Therefore, in this modified example, a positional relationship between the second lens portion 11b and the wiring 12 is fixed within the detection head 3, and the contact terminal 15 of the wiring 12 is disposed outside the imaging view field of the photography unit 9.

The second lens portion 11b can also function as a lid for closing the opening on the proximal end side of the detection head 3, thereby it is possible to prevent dust or the like from entering the detection head 3. Therefore, an additional configuration such as a cover ballast for preventing dust from entering the detection head 3 becomes unnecessary, and a manufacturing cost of the inner surface shape measurement device can be reduced. Similarly, in the insertion portion 2, the first lens portion 11a can also function as a lid closing the opening of the distal end of the insertion portion 2, thereby it is possible to prevent dust or the like from entering the insertion portion 2.

In this modified example, the detection head 3 and the insertion portion 2 are detachable. Therefore, a task can be easily performed by exchanging the detection head 3 in a case in which the detection head 3 fails, a case in which the imaging view field of the photography unit 9 is changed, or the like. In addition, an inner surface shape measurement device including a plurality of detection heads 3 having different optical characteristics can be achieved. In this case, it is possible to perform suitable measurement and observation under a variety of environments. For example, when the test target T is a tube, the detection head 3 can be replaced to correspond to inner-diameter dimensions of the tube.

Further, it is possible to achieve the detection head 3 capable of being attached to a distal end of a general direct-view type endoscope and photographing the entire circumference of the inner surface of the test target T by disposing a portion (the second lens portion 11b) of the objective optical system 11 in the detection head 3.

Modified Example 3-1

Figure 9:
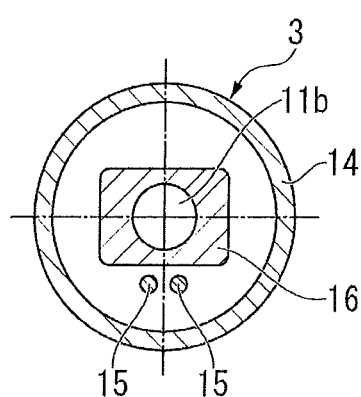
FIG. 9 is a cross-sectional view illustrating a modified example of the inner surface shape measurement device according to the third embodiment of the present invention.
Figure 10:
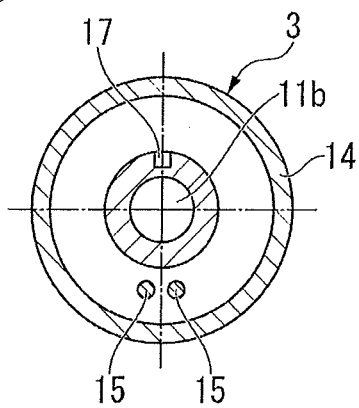
FIG. 10 is a cross-sectional view illustrating another configuration example of the modified example of the inner surface shape measurement device according to the third embodiment of the present invention.

Next, a modified example of the inner surface shape measurement device according to the third embodiment described above will be described. FIGS. 9 and 10 are cross-sectional views illustrating the inner surface shape measurement device of this modified example, and are views illustrating cross-sections taken along the line A-A of FIG. 7.

This modified example is different from the third embodiment described above in a configuration for performing positioning in a circumferential direction of the detection head 3 and the insertion portion 2.

For example, an optical axis of the objective optical system 11 may be set on the central axis line of the head frame 4, and a concavo-convex part having a predetermined shape (e.g., a concavo-convex portion 16 having a corner-rounded rectangular shape) surrounding the second lens portion 11b may be provided at the detection head 3, as illustrated in FIG. 9. In this case, if a concavo-convex part fit to the concavo-convex part formed in the detection head 3 is formed in the insertion portion 2, the detection head 3 and the insertion portion 2 can be positioned in the circumferential direction.

Further, for example, a pin 17 may be provided at a lens barrel which holds the second lens portion 11b, and a hole into which this pin 17 is inserted may be provided on the distal end of the insertion portion 2, as illustrated in FIG. 10. In this case, the detection head 3 and the insertion portion 2 can be positioned in the circumferential direction as well.

In this modified example, when it is necessary to perform measurement in a state that the central axis line of the objective optical system 11 is aligned a central axis line of a tube, for example, in a case in which the test target T is the tube, the central axis lines can be easily positioned.

Modified Example 3-2

Next, another modified example of the inner surface shape measurement device according to this embodiment will be described. FIGS. 11 to 14 are schematic views illustrating the inner surface shape measurement device of this modified example.

This modified example is different from the third embodiment in components disposed in the detection head 3 and components disposed in the insertion portion 2.
(Configuration 1)

Figure 11:
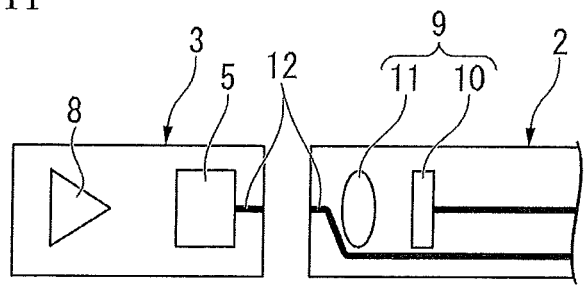
FIG. 11 is a schematic view illustrating another modified example of the inner surface shape measurement device according to the third embodiment of the present invention.

For example, the optical system 8, the light source 5 and a portion of the wiring 12 may be disposed within the detection head 3, and the objective optical system 11 and the image sensor 10 may be disposed within the insertion portion 2, as illustrated in FIG. 11. In this case, the proximal end of the wiring 12 connected to the light source 5 and the distal end of the wiring 12 arranged on the insertion portion 2 side extend along the optical axis of the objective optical system 11, and are detachable from each other.
(Configuration 2)

Figure 12:
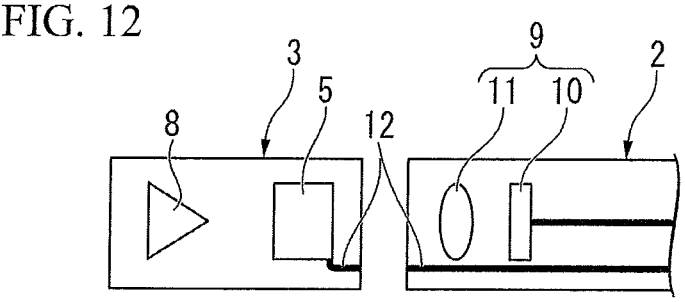
FIG. 12 is a schematic view illustrating another configuration example of the modified example of the inner surface shape measurement device according to the third embodiment of the present invention.

For example, the optical system 8, the light source 5, and a portion of the wiring 12 may be disposed in the detection head 3, and the objective optical system 11 and the image sensor 10 may be disposed within the insertion portion 2, as illustrated in FIG. 12. In this configuration, the wiring 12 extends along an inner circumferential surface of the head frame 4 and the insertion portion 2, and has optical transparency.
(Configuration 3)

Figure 13:
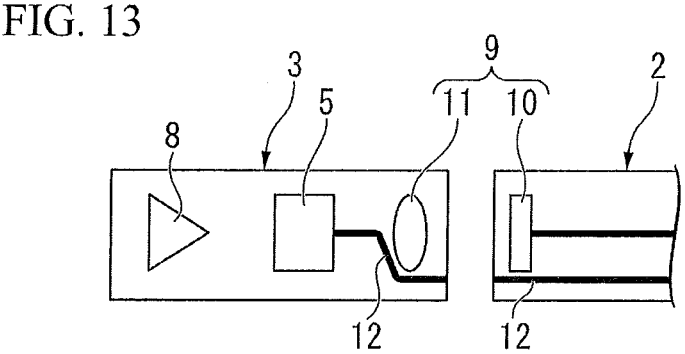
FIG. 13 is a schematic view illustrating another configuration example of the modified example of the inner surface shape measurement device according to the third embodiment of the present invention.

For example, the optical system 8, the light source 5, the objective optical system 11, and a portion of the wiring 12 may be disposed in the detection head 3, and the image sensor 10 may be disposed within the insertion portion 2, as illustrated in FIG. 13.
(Configuration 4)

Figure 14:
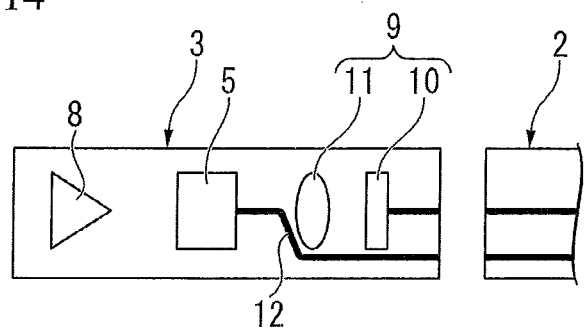
FIG. 14 is a schematic view illustrating another configuration example of the modified example of the inner surface shape measurement device according to the third embodiment of the present invention.

For example, the optical system 8, the light source 5, the objective optical system 11, and the image sensor 10 are disposed in the detection head 3, and a portion of the wiring 12 and a portion of a signal line of the image sensor 10 may be disposed within the insertion portion 2, as illustrated in FIG. 14.

The same effects as those in the inner surface shape measurement device according to the third embodiment described above are achieved by each configuration described above.

While preferred embodiments of the present invention have been described and illustrated above, it should be understood that these are exemplary of the present invention and are not to be considered as limiting. Additions, omissions, substitutions, and other modifications can be made without departing from the spirit or scope of the present invention. Accordingly, the present invention is not to be considered as being limited by the foregoing description, and is only limited by the scope of the appended claims.

What is claimed is:

1. An inner surface shape measurement device for measuring a shape of an inner surface of a test target, the inner surface shape measurement device comprising:
    a light source;
    an optical system that converts a light beam irradiated toward the inner surface;
    an imaging sensor that has a central axis line and acquires an image of an imaging view of the light beam projected to the inner surface; and
    a wiring that supplies a power for driving the light source,
    wherein the optical system, the light source and the imaging sensor are disposed in this order along the central axis line,
    the light source includes a measurement light source that emits a measurement light toward the optical system, and an illumination light source that emits an illumination light for causing the imaging sensor to capture a bright field image of the inner surface, the wiring includes a wiring for the measurement light source and a wiring for the illumination light source, the wiring includes a first straight portion, a first bent portion, a second straight portion, and a second bent portion in this order, the first straight portion is disposed between the light source and the imaging sensor along the central axis line, the first bent portion is disposed at an imaging-sensor-side of the first straight portion, the second straight portion is disposed to extend across an imaging view field, and the second bent portion is disposed outside of the imaging view field.

2. The inner surface shape measurement device according to claim 1, wherein the imaging sensor includes an objective optical system, the first straight portion of the wiring extends from the light source toward the imaging sensor along the central axis line, the first bent portion of the wiring is disposed at an adjacent position of the imaging sensor, and the second straight portion of the wiring extends in a direction intersecting the central axis line.

3. The inner surface shape measurement device according to claim 2, wherein a distance between the objective optical system and the first bent portion is shorter than a focused focal point distance of the objective optical system.

4. The inner surface shape measurement device according to claim 3, wherein the focused focal point distance of the objective optical system is larger than a distance between the light source and the objective optical system.

5. The inner surface shape measurement device according to claim 2, further comprising:

a cylindrical member including an imaging-sensor-side opening disposed at a position apart from the imaging sensor by a predetermined distance and a light-source-side opening opened to the light source, the imaging-sensor-side opening being fixed to the light source, wherein a central axis line of the cylindrical member extends along the central axis line of the imaging sensor, and the wiring is inserted into the cylindrical member.

6. The inner surface shape measurement device according to claim 5, wherein a position of the first bent portion is the same as a position of the imaging-sensor-side opening.

7. The inner surface shape measurement device according to claim 2, wherein the wiring has optical transparency in a range of a view field of the imaging sensor.

8. The inner surface shape measurement device according to claim 2, further comprising:

an insertion portion inserted into the test target, wherein the insertion portion includes:

a cylindrical-shape main body; and a detection head detachably provided at an end portion of the cylindrical-shape main body, the light source and the optical system being disposed inside the detection head.

9. The inner surface shape measurement device according to claim 8, wherein at least a part of optical components constituting the objective optical system is disposed inside the detection head.

10. The inner surface shape measurement device according to claim 2, wherein the illumination light source has an optical axis directed in a direction in which the central axis line extends.

11. The inner surface shape measurement device according to claim 10, wherein the illumination light source emits the illumination light toward the optical system, and the optical system reflects the illumination light in a direction intersecting a direction in which the central axis line extends.

12. The inner surface shape measurement device according to claim 11, wherein the optical system includes a proximal end portion having a conical shape and a distal end having a curved shape.

13. The inner surface shape measurement device according to claim 2, wherein the illumination light source emits the illumination light in a direction intersecting a direction in which the central axis line extends.

14. A detection head which is attachable to a distal end of an insertion portion of an endoscope in order to measure a shape of an inner surface of a test target, the detection head comprising:

a light source;

an optical system that converts a light beam irradiated toward the inner surface;

an imaging sensor that has a central axis line and acquires an image of an imaging view of the light beam projected to the inner surface; and a wiring that supplies a power for driving the light source, wherein the optical system, the light source and the imaging sensor are disposed in this order along the central axis line, the light source includes a measurement light source that emits a measurement light toward the optical system, and an illumination light source that emits an illumination light for causing the imaging sensor to capture a bright field image of the inner surface, the wiring includes a wiring for the measurement light source and a wiring for the illumination light source, the wiring includes a first straight portion, a first bent portion, a second straight portion, and a second bent portion in this order, the first straight portion is disposed between the light source and the imaging sensor and extends along the central axis line, the first bent portion is disposed at an imaging-sensor-side of the first straight portion, the second straight portion is disposed to extend across an imaging view field of the imaging sensor, and the second bent portion is disposed outside of the imaging view field.

15. The detection head according to claim 14, wherein the wiring has a contact terminal that electrically connects to the distal end of the insertion portion, and the contact terminal is disposed outside of an imaging view field of the imaging sensor.

16. A detection head which is attachable to a distal end of an insertion portion of an endoscope in order to measure a shape of an inner surface of a test target, an imaging sensor being disposed inside the distal end of the insertion portion, the detection head comprising:
- a light source;
- an optical system that converts a light beam irradiated toward the inner surface; and
- a wiring that supplies a power for driving the light source,
- wherein, in a state in which the detection head is attached to the distal end of the insertion portion, the optical system and the light source are disposed so that the optical system, the light source and the imaging sensor are in this order along a central axis line of the imaging sensor,
- the light source includes a measurement light source that emits a measurement light toward the optical system, and an illumination light source that emits an illumination light for causing the imaging sensor to capture a bright field image of the inner surface,
- the wiring includes a wiring for the measurement light source and a wiring for the illumination light source,
- the wiring includes a first straight portion, a first bent portion, a second straight portion, and a second bent portion in this order, and
- in a state in which the detection head is attached to the distal end of the insertion portion,
- the first straight portion is disposed between the light source and the imaging sensor and extends along the central axis line of the imaging sensor,
- the first bent portion is disposed at an imaging-sensor-side of the first straight portion,
- the second straight portion is disposed to extend across an imaging view field of the imaging sensor, and
- the second bent portion is disposed outside of the imaging view field.

17. The detection head according to claim 16, wherein the wiring has a contact terminal that electrically connects to the distal end of the insertion portion, and the contact terminal is disposed outside of an imaging view field of the imaging sensor.

18. The detection head according to claim 16, further comprising:
a positioning portion that positions the detection head and the insertion portion around the central axis line.

* * * * *